US00PP14177P39

(12) United States Plant Patent
Leis et al.

(10) Patent No.: US PP14,177 P3
(45) Date of Patent: Sep. 23, 2003

(54) APPLE TREE NAMED 'CIVNI'

(75) Inventors: Michelangelo Leis, Ferrara (IT); Gianfranco Castagnoli, Quingentole (IT); Alessio Martinelli, Gaibanella (IT)

(73) Assignee: C.I.V. Consorzio Italiano Vivaisti, Giuseppe di Commachio (IT)

( * ) Notice: Subject to any disclaimer, the term of this patent is extended or adjusted under 35 U.S.C. 154(b) by 0 days.

(21) Appl. No.: 10/014,576

(22) Filed: Dec. 14, 2001

(65) Prior Publication Data

US 2003/0115647 P1 Jun. 19, 2003

(30) Foreign Application Priority Data

Dec. 14, 2000 (EP) ..... 2000/1892

(51) Int. Cl.[7] ..... A01H 5/00
(52) U.S. Cl. ..... Plt./161
(58) Field of Search ..... Plt./161

*Primary Examiner*—Bruce R. Campell
*Assistant Examiner*—Susan B. McCormick
(74) *Attorney, Agent, or Firm*—Foley & Lardner

(57) ABSTRACT

A new variety of apple tree named 'Civni' characterized by high sugar content, no biennial bearing (bears regularly every year), semi-spur plant and firm, crisp, juicy and aromatic fruit.

4 Drawing Sheets

Latin name of the genus and species of the plant claimed: *Malus domestica* Borkh.
Variety denomination: Civni.

BACKGROUND OF THE INVENTION

The present invention comprises a new and distinct apple tree cultivar of Malus Mill., hereinafter referred to by the cultivar name 'Civni'. This new and distinct cultivar was bred by inventors Michelangelo Leis, Gianfranco Castagnoli and Alessio Martinelli in Ferrara, Italy, in search of a variety which is of dessert quality, with higher acidity and longer storage capability than that of the 'Gala' variety, but with lower acidity than that of the 'Elstar' variety. The new cultivar is a cross between the varieties 'Elstar' ('Golden Delicious'×'Ingrid Marie'—1955) and 'Gala' ('Kidd's Orange'×'Golden Delicious'—1939).

BRIEF DESCRIPTION OF THE INVENTION

The following traits have been repeatedly observed and are determined to be basic characteristics of 'Civni' which in combination distinguish this apple tree as a new and distinct cultivar:

1. high sugar content;
2. no biennial bearing (bears regularly every year);
3. semi-spur plant; and
4. firm, crisp, juicy and aromatic fruit.

'Civni' has not been observed under all possible environmental conditions. The phenotype of the new cultivar may vary significantly with variations in environment such as temperature, light intensity, and day length without any change in genotype. The new cultivar reproduces true to type.

In comparison to the parental cultivar, 'Gala', 'Civni' has thicker, more elastic leaves which fold, whereas the leaves of 'Gala' break more easily when folded. 'Civni' is smaller in average plant height and spread, and has a smaller trunk diameter. The measurements in Table 1 were taken of 8 year old trees which had been equally pruned annually; trunk diameter was measured 10 cm above above the point of grafting.

TABLE 1

| Variety | Average height | Average spread | Trunk Diameter |
|---|---|---|---|
| 'Gala' | 336 | 273 | 119 |
| 'Civni' | 236 | 200 | 85.9 |

BRIEF DESCRIPTION OF THE DRAWINGS

The following drawings are photographs of 'Civni' taken in Cuneo, Italy during the growing season 2001.

The first drawing is a view of a blooming tree.

The second drawing is a view of the inflorescence.

The third drawing is a view of fruit-bearing trees.

The fourth drawing is a close view of two fruits.

DETAILED BOTANICAL DESCRIPTION

Color references are made to The Royal Horticultural Society Colour Chart (R.H.S.), except where general colors of ordinary significance are used.

The following is a detailed description of the invention based on 8 year old plants that were grown in Cuneo, Italy in the experimental farm of a fruit growers association located at 550 meters above sea level, and observed at that location between 1997–2001 unless otherwise indicated. All trees were of cropping maturity. For comparison purposes, except as noted below, fruit from all the strains as noted were grown at Cuneo, Italy and were from trees of similar age.

Color varies significantly with growing conditions and locations. For example the fruit has been observed to be more orange in color when grown in hotter growing conditions, and more red in color when grown under cooler conditions. Also the amount of red color varies, being more extended in cooler areas. Climate and horticultural practices affect fruit length: fruits are longer in cooler areas. Soil conditions, such as the amount of nitrogen in the soil, affects fruit color and also leaf color. Colors are also affected by the amount of sunlight received by the fruit as the fruit matures, with fruit growing in shaded areas inside of a tree having less red color.

All trees of 'Civni', insofar as they have been observed, have been identical in all the characteristics described below.

Propagation: Holds to distinguishing characteristics through succeeding asexual propagations by budding and grafting.

*Locality where grown and observed.*—Cuneo, Italy (except as otherwise noted).

*Dates of first and last picking.*—The first pick was Aug. 31, 2000, last pick was Sep. 8, 2000. First picking of the variety 'Gala' in the same farm in 2000 was August 22 and last picking was August 30.

Tree:

*Vigor.*—Medium, 30% less vigorous then the 'Gala' variety (seeTable 1); in the years 2000 to 2002, 'Civni' increased in growth 54.3%.

*Habit.*—Upright, good ramification, branches angle is about 50° with respect to trunk.

*Branches.*—Average length 255 mm; average diameter 5.5 mm; color RHS 201A; smooth texture.

*Trunk.*—Diameter 85.9 mm as measured 10 cm above point of grafting; bark texture is smooth; RHS 197A in color.

*Predominance of bearing.*—On spur.

*Dormant one year shoot.*—Internode lengths of about 2.8 cm and width of about 6 mm, medium pubescence. Lenticels: pale brown, RHS 165D; average number on an area of 5 $cm^2$ is 27.65; average length is 1.42 mm; average width 0.9 mm.

*Pruning.*—Similar to the 'Gala' variety with weaker vegetation. Requires regular renewal of fruiting branches and shoots. Does well as a slender spindle. High flower numbers preferably reduced by regular pruning and fruit thinning.

Leaves (1 year old shoot, average of 50 typical leaves):

*Size.*—Medium (length/width ratio 1.89);110 mm long and 58 mm wide.

*Shape.*—Elliptical-elongated and slightly undulated, with serrate margin and acute apex and base shape.

*Petiole.*—Average40.5 mm in length and 1.88 mm in diameter, green in color RHS 137B.

*Color.*—Green to pale green, medium glossy. Varies with growing conditions. Leaves observed in early summer in 2001 growing season had an upper leaf surface color closest to RHS 137B, lower leaf surface RHS 138D.

*Veins.*—Prominent veination from the central vein to the leaf edge; color RHS 138 D.

Spurs:

*Size.*—Smaller then the leaves of one year old shoot (length/width ratio 2.18). In one observation, in early summer, the leaves were 96 mm long and 44 mm wide (high variance).

*Shape.*—Elliptical-elongated.

*Petiole.*—42 mm long and of medium thickness.

*Color.*—Closest to RHS 137B.

Inflorescence: Blooms regularly and abundantly; full blooming each year.

*Size.*—Medium.

*Color.*—Red-purple to pink-white. Open flower, white, with red-purple to pink, RHS 63B.

*Petals.*—Five.

*Buds.*—Average length 8.81 mm; average diameter 4.5 mm; color RHS 200B.

*Pistil-stigma.*—Bulbous on top.

*Anthers.*—13 to 15 in a single row; pale yellow in color RHS 8B.

*Fragrance.*—Very slight.

*Flowering period.*—Mid-season, like 'Gala' (average of observations in Cuneo, Italy in the years 1997–2000). Full bloom of 'Civni' in the 2000 growing season occurred on April 18, while for 'Gala' on April 16.

*Pollination.*—The new variety is a good pollinator for all the varieties that bloom in the same season as 'Gala'; it is well pollinated by 'Gala' and Golden Delicious.

Fruit:

*Size.*—Medium to large; thirty typical fruit grown during the 2000 growing season averaged 229 grams in weight, had a diameter 82.03 mm. Fruit size will vary with the growing season and the extent to which the tree is thinned.

*Shape.*—Conical-truncated, height/thickness ratio= 0.915, (Baldini) slightly asymmetrical.

*Calyx basin.*—Deep 13.1 mm, large 33.0 mm; sepals medium 5.3 mm, convergent and free.

*Calyx.*—Half-open, from medium to large maximum width 9.2 mm.

*Stalk basin.*—Deep 16.8 mm and large 22.5 mm. There is a slightly russet around cavity (RHS 137C).

*Stalk.*—Length 23.1 mm, diameter 3.7 mm; the protrusion of the stalk is significantly beyond cavity. Stalk color RHS 172B.

*Skin.*—The surface texture is smooth, the skin is dry, slightly waxy when overripe, and the thickness is medium (comparable to 'Gala'). Color: ground color: green/yellow, RHS 5C. Varies with growing conditions, RHS 5C in one observation of fruit at full maturity. Over color: red to vermilion (60 to 100%) RHS 33A or 34A in one observation of fruit at full maturity. Color markings: dark red stripes, RHS 45A. Overall: Very attractive bright red to red-orange, RHS 33B. Lenticels: Medium, comparable to 'Gala'. Color and quantity of lenticels: brown and rather numerous.

*Flesh.*—Firm and juicy, sweet, aromatic and of medium texture. The cavity beneath the eye is Y shaped. Color of flesh, typically a creamy white, RHS 11D. Pressure 7–9 Kg typical, soluble solids 14–15° brix typical. Firmness keeps very well in storage.

*Core.*—Rather symmetrical. Distinctness of core lines: strong. Calyx tube: narrow. Cells: closed. Seeds: Number in one cell: 2. Measurement of 30 seeds collected from ripened fruits in 2001 averaged: length 8.15 mm; width 4.75 mm, diameter 2.84 mm. Color: brown closest to RHS 165A, in ripened fruit.

The following table summarizes the comparison of fruits of the invention with fruits of 'Gala' grown in Cuneo Italy in year 2000. Trees were of the same age (planted in March 1996). Thirty fruits per variety were measured.

TABLE 2

| Variety | Weight (g/fruit) | Caliper (mm/fruit) | Over-color | Flesh firmness (Kg/0.5 $mm^2$) | Brix | Acidity (meq) |
|---|---|---|---|---|---|---|
| 'Gala' | 203.87 | 76.33 | 94.5 | 9.67 | 12.84 | 5.5 |
| Civni | 233.6 | 82.5 | 89.83 | 8.08 | 13.89 | 9.6 |

*Quality.*—Excellent. Flavor good, sugar-acid balance excellent.

*Use.*—Suitable as dessert apple from September to May in Italy.

*Storage.*—Keeps well in both common cold storage (until March) and in controlled atmosphere (until May). Less storage losses than 'Gala'.

*Yield.*—Very productive, bears regularly every year (no alternate bearing). Precocious, bearing on one-year-old shoots. Does well on 'M 9' rootstocks.

*Ploidy.*—Diploid with good viable pollen.

*Winter hardiness.*—Tolerance to −10° C. without observed damage to plant.

*Drought/heat tolerance.*—Tolerance to temperatures over 40° C. without observed damage to plant.

*Resistance to insects and disease.*—Susceptible to scab and slightly susceptible to powdery mildew.

I claim:

1. A new and distinct variety of apple tree named 'Civni' as substantially described and illustrated herein.

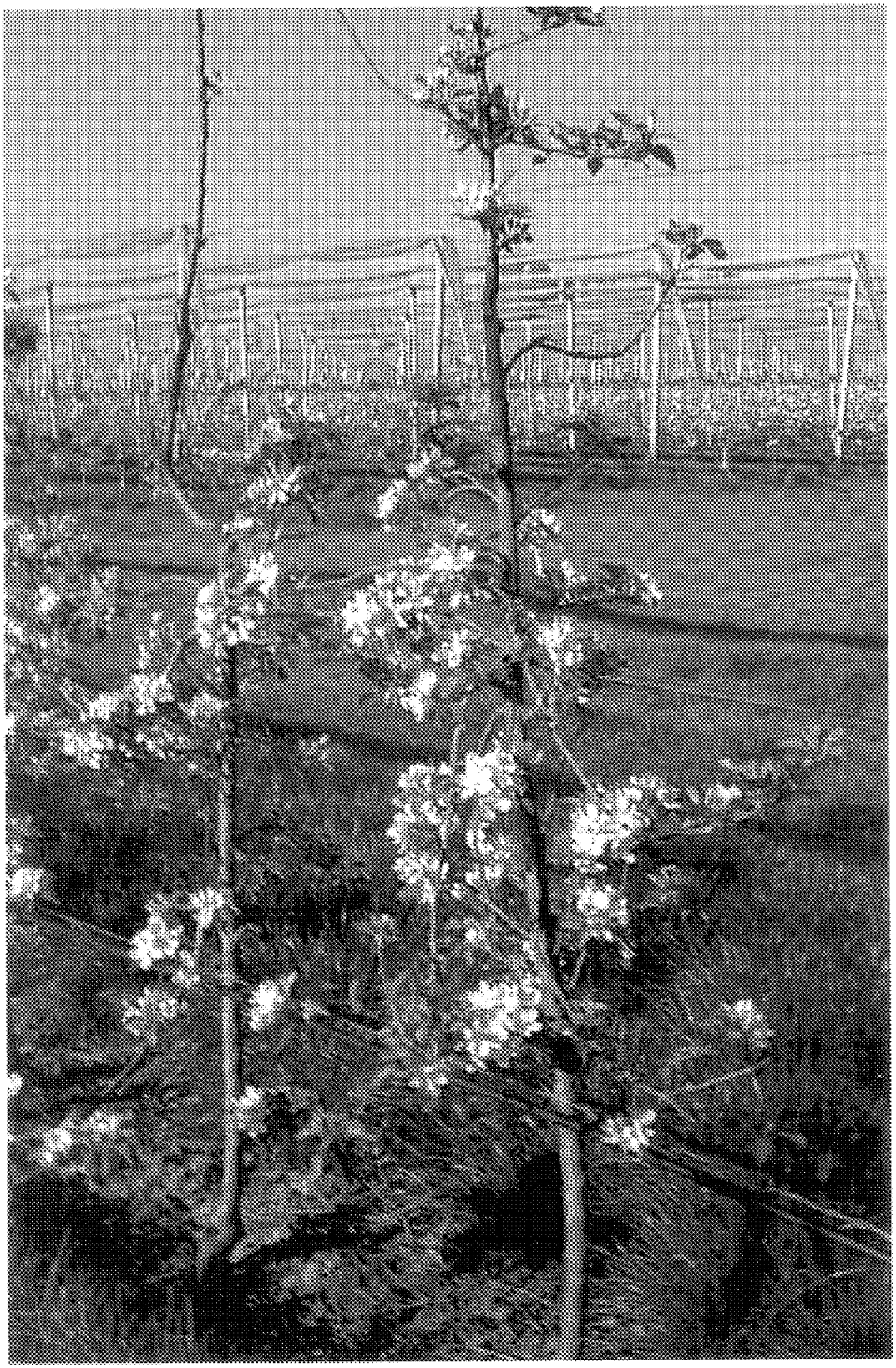

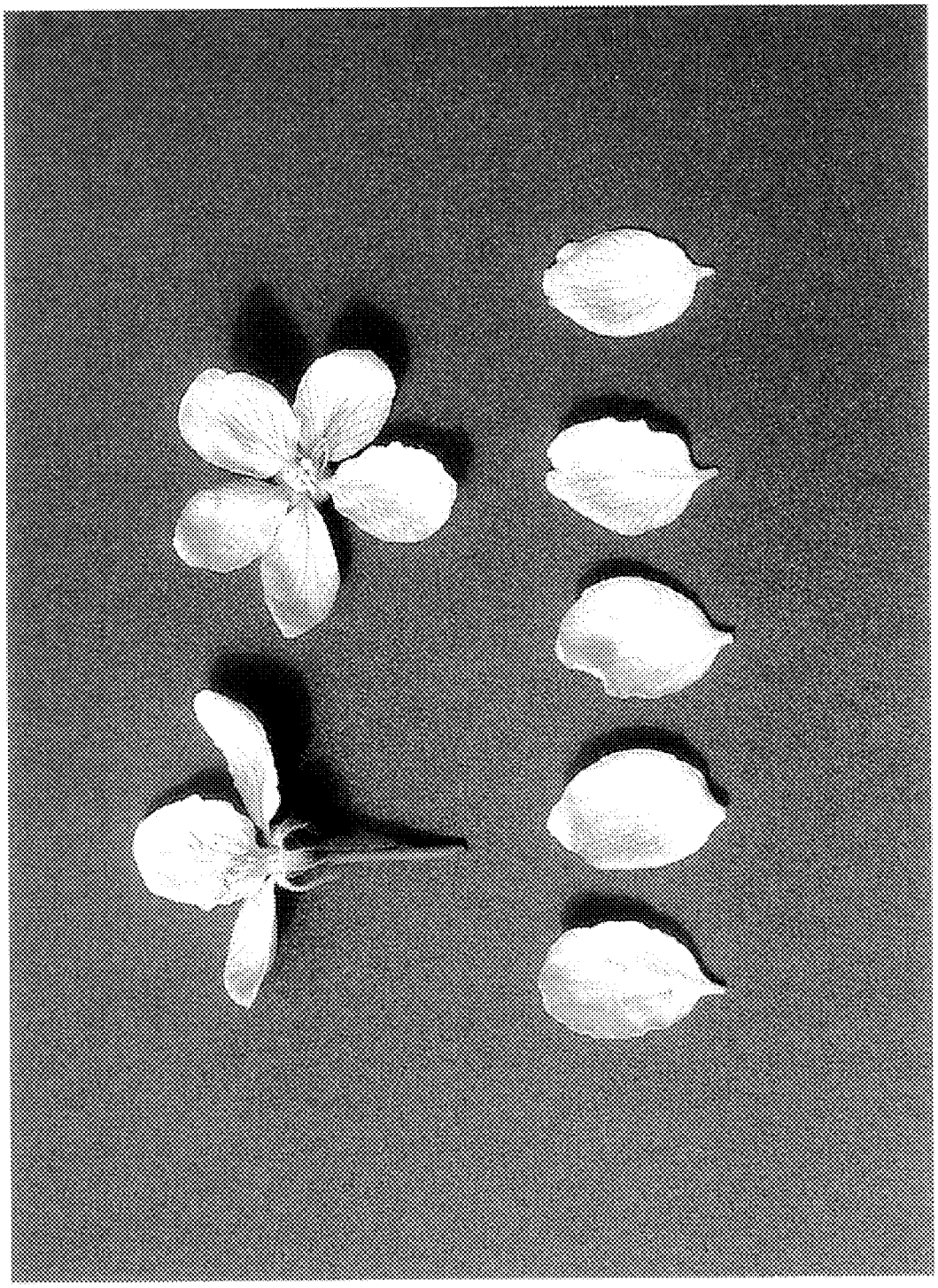

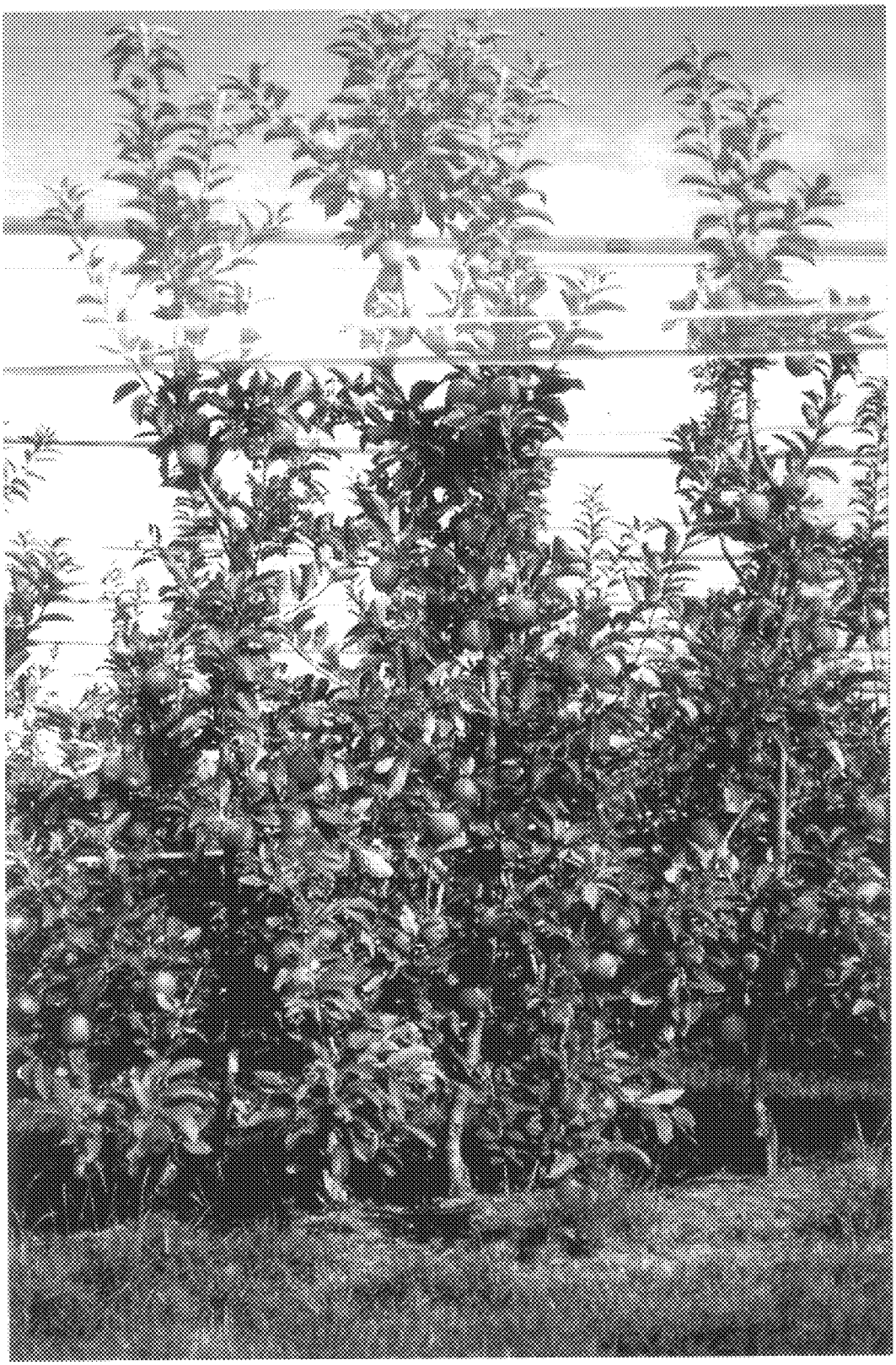

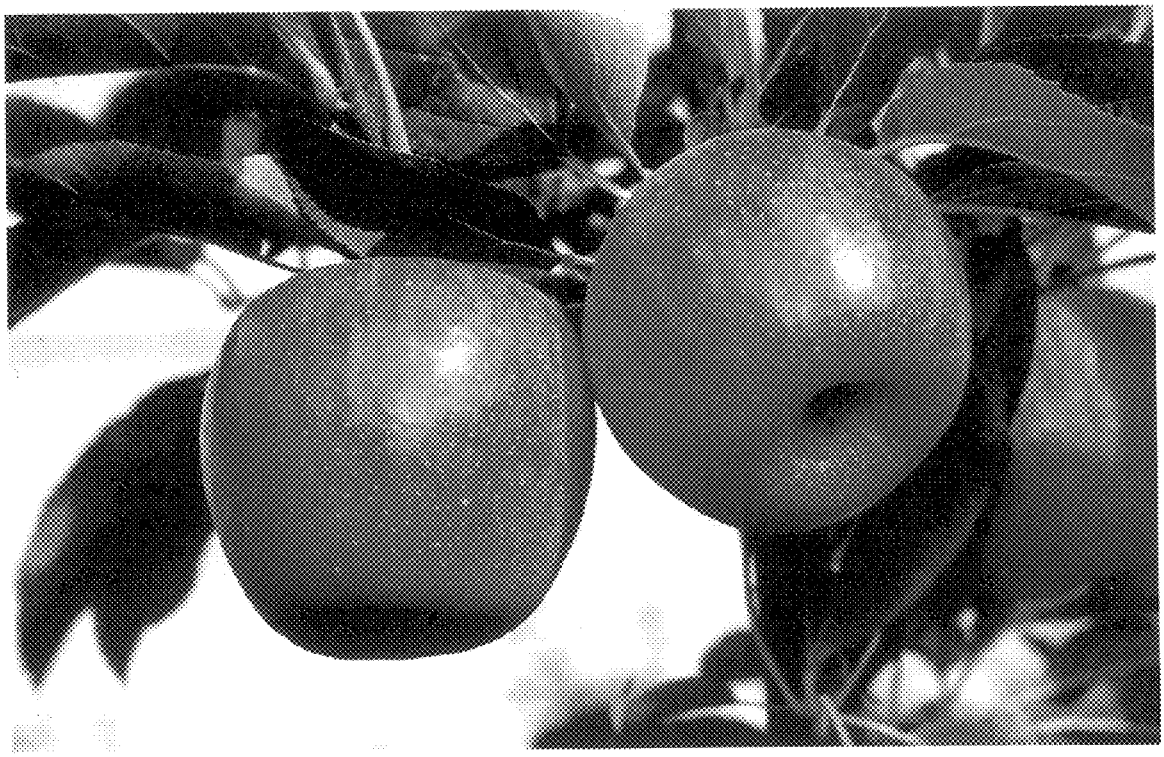

* * * * *